(12) United States Patent
Sauzade et al.

(10) Patent No.: US 8,869,791 B2
(45) Date of Patent: Oct. 28, 2014

(54) FLUID PRODUCT DISPENSING DEVICE

(75) Inventors: Jean-Denis Sauzade, Grace (FR);
Pascal Bruna, Sotteville les Rouen (FR)

(73) Assignee: Aptar France SAS, Le Neubourg (FR)

( * ) Notice: Subject to any disclaimer, the term of this patent is extended or adjusted under 35 U.S.C. 154(b) by 1600 days.

(21) Appl. No.: 10/583,256

(22) PCT Filed: Dec. 16, 2004

(86) PCT No.: PCT/FR2004/050706
§ 371 (c)(1),
(2), (4) Date: Apr. 6, 2007

(87) PCT Pub. No.: WO2005/061998
PCT Pub. Date: Jul. 7, 2005

(65) Prior Publication Data
US 2007/0240707 A1   Oct. 18, 2007

(30) Foreign Application Priority Data
Dec. 19, 2003   (FR) ...................................... 03 15040

(51) Int. Cl.
*A61M 11/00*   (2006.01)
*G01F 13/00*   (2006.01)

(52) U.S. Cl.
CPC ................................... *G01F 13/008* (2013.01)
USPC .................................................. 128/200.14

(58) Field of Classification Search
USPC ............. 128/200.14, 200.23, 204.21, 205.23;
222/33, 30, 41, 321.2; 73/730, 721,
73/727, 753, 754
See application file for complete search history.

(56) References Cited

U.S. PATENT DOCUMENTS

| 3,603,152 | A | * | 9/1971 | Alibert et al. | 73/723 |
| 4,179,939 | A | * | 12/1979 | Price | 73/730 |
| 4,194,401 | A | * | 3/1980 | Claassen et al. | 73/730 |
| 4,296,635 | A | * | 10/1981 | Claassen et al. | 73/730 |
| 4,775,816 | A | * | 10/1988 | White et al. | 310/338 |
| 4,972,830 | A | * | 11/1990 | Wong et al. | 128/200.21 |
| 5,284,133 | A | | 2/1994 | Burns et al. | |
| 5,415,161 | A | | 5/1995 | Ryder | |
| 5,433,342 | A | | 7/1995 | Luro | |
| 5,544,647 | A | * | 8/1996 | Jewett et al. | 128/200.23 |
| 5,676,129 | A | * | 10/1997 | Rocci et al. | 128/200.23 |
| 5,809,997 | A | * | 9/1998 | Wolf | 128/200.23 |
| 6,119,684 | A | | 9/2000 | Noehl et al. | |
| 6,129,702 | A | | 10/2000 | Wolas et al. | |
| 6,138,669 | A | | 10/2000 | Rocci et al. | |
| 6,148,815 | A | * | 11/2000 | Wolf | 128/205.23 |

(Continued)

FOREIGN PATENT DOCUMENTS

GB   2 116 314 A   9/1983
GB   2266466 A * 11/1993

(Continued)

*Primary Examiner* — Justine Yu
*Assistant Examiner* — LaToya M Louis
(74) *Attorney, Agent, or Firm* — Sughrue Mion, PLLC

(57) ABSTRACT

A fluid dispenser device including a fluid dispenser member (10) such as a pump or a valve, and a dispenser head (20) provided with a dispensing orifice, the fluid dispenser device is provided with dispensing detector mechanism (30, 31) for detecting dispensing of a dose of fluid, the detector mechanism (30, 31) adapted to deliver a signal for informing the user that a dose of fluid has indeed been dispensed by the pump, the detector mechanism including a detector (30) for detecting the fluid going from the dispenser member to the dispenser orifice.

14 Claims, 3 Drawing Sheets

(56) References Cited

U.S. PATENT DOCUMENTS

| | | | |
|---|---|---|---|
| 6,170,482 B1 * | 1/2001 | Howlett | 128/200.23 |
| 6,353,324 B1 * | 3/2002 | Uber et al. | 324/457 |
| 6,651,651 B1 * | 11/2003 | Bonney et al. | 128/200.23 |
| 6,684,879 B1 * | 2/2004 | Coffee et al. | 128/200.14 |
| 7,168,597 B1 | 1/2007 | Jones et al. | 222/402.2 |
| 7,347,200 B2 * | 3/2008 | Jones et al. | 128/200.23 |
| 2004/0252290 A1 | 12/2004 | Ferguson et al. | |

FOREIGN PATENT DOCUMENTS

| | | |
|---|---|---|
| GB | 2 304 327 A | 3/1997 |
| WO | WO 9419042 A1 * | 9/1994 |
| WO | 02/36190 A2 | 5/2002 |
| WO | WO 02/070047 A | 9/2002 |

* cited by examiner

FLUID PRODUCT DISPENSING DEVICE

The present invention relates to a fluid dispenser device, and more particularly to such a device that includes a pump or a valve that is actuated manually.

It is known that pumps or valves can be used for dispensing fluid (liquid, cream, or powder) in metered quantities or "doses", in particular in the fields of pharmaceuticals, of perfumes, and of cosmetics. In particular in the field of pharmaceuticals, it can be very important to avoid any risk of over-dosing and/or of under-counting. With a valve, operating by means of a propellant gas, the problem relates above all to counting the number of doses delivered, and it is often necessary to avoid any risk of under-counting so that the user is not left with an empty device when said user believes that a few doses remain to be dispensed. Counting systems are generally associated with such valves so as to count the doses delivered, said systems generally being actuated by the reservoir and the valve member of the valve moving relative to each other. Problems can arise in the event of partial or interrupted actuation, which can cause doses to be expelled, partially or fully. Complicated counters have been proposed to take account of this problem, but, in order to be reliable, they must be highly complex and therefore very costly. When a pump is used, and in particular when a new-generation pump is used, another problem can arise in addition to the risk of under-counting. The spray can be so fine that the user is not always aware that the dose has been dispensed. This applies particularly with certain nasal dispenser pumps. In which case, no indication is given to the user that the dose has indeed been dispensed, and there is a risk that the user might actuate the device again, thinking that the first actuation had been ineffective. That gives rise to a risk of over-dosing, which can be detrimental to the health of the user.

An object of the present invention is to provide a fluid spray device that does not reproduce the above-mentioned drawbacks.

A particular object of the present invention is to provide a fluid spray device having a pump or a valve that avoids any risk of over-dosing and/or of under-counting the delivered doses.

An object of the present invention is also to provide such a device that is simple and inexpensive to manufacture and to assemble, and that is safe and reliable to use.

The present invention thus provides a fluid dispenser device including a fluid dispenser member such as a pump or a valve, and a dispenser head provided with a dispensing orifice, said fluid dispenser device being characterized in that said device is provided with dispensing detector means for detecting dispensing of a dose of fluid, said detector means being adapted to deliver a signal for informing the user that a dose of fluid has indeed been dispensed by said pump, said detector means comprising a detector for detecting the fluid going from said dispenser member to said dispenser orifice.

Advantageously, the dispenser member is connected to the dispensing orifice via an expulsion channel, said detector means being provided in said expulsion channel.

Advantageously, said detector comprises a dynamic pressure detector.

In a first embodiment, said detector comprises a piezoelectric material.

Advantageously, said detector comprises polyvinylidene fluoride (PVDF).

Advantageously, said detector comprises a PVDF tube operating in breathing mode.

Advantageously, said PVDF tube is disposed around a portion of said expulsion channel.

In a second embodiment, said detector comprises an optical fiber.

Advantageously, said optical fiber is associated with a deformable membrane which deforms when fluid passes through it, such deformation generating stress in the optical fiber.

Advantageously, said deformable membrane is disposed around a portion of said expulsion channel.

Advantageously, said optical fiber co-operates with said deformable membrane in a casing secured to the dispenser head.

Advantageously, said optical fiber is made of plastic or of glass.

Advantageously, said detector means are disposed in a sleeve co-operating at one end with said dispenser member and at the other end with said dispenser head.

Advantageously, said sleeve is made up of two portions engaged one on and/or around the other, said detector means being disposed between said two sleeve portions.

Advantageously, said sleeve is engaged around the valve member of the valve, or around the actuator rod of the pump.

Advantageously, said detector means are connected to electronic means for processing the signals delivered by said detector.

Advantageously, said detector means are adapted to increment or to decrement a dose counter.

Advantageously, said dispenser member is a pump adapted to dispensing the fluid such that it is so finely sprayed that the spray is undetectable by the user, said detector means informing the user every time a dose of fluid is dispensed.

In a variant, said dispenser member is a metering valve operating with a propellant gas.

Other characteristics and advantages of the present invention appear more clearly from the following detailed description given with reference to the accompanying drawings, which are given by way of non-limiting example, and in which.

Figure 1:
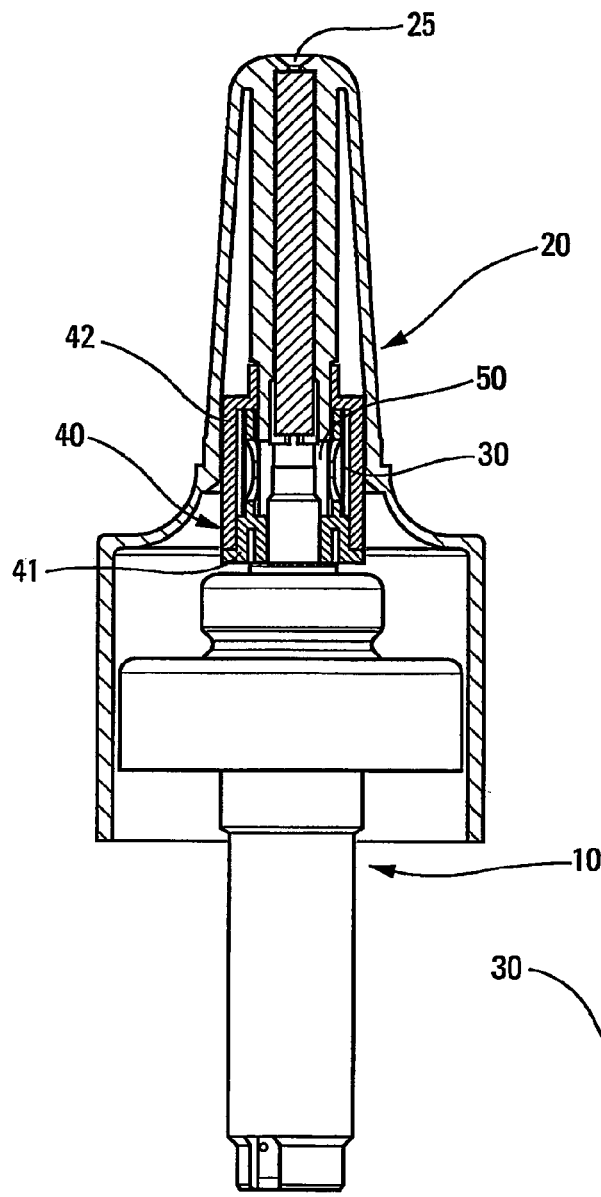
FIG. 1 is a diagrammatic section view of a first embodiment of a spray device of the present invention.

FIG. 1 shows a dispenser member that is a pump 10 to which a dispenser head 20 provided with a dispensing orifice 25 is assembled. The pump can be of any type, and the internal structure of the pump is thus not described in any further detail below. The present invention is particularly but not exclusively applicable to dispenser pumps that are adapted to dispense a dose of fluid in the form of a very fine spray each time they are actuated. The dispenser head 20 shown in FIG. 1 is a nasal dispenser head, and it is used for manually actuating the pump 10. Naturally, the present invention is not limited to the example shown in the figure, and a variety of embodiments can be devised. The pump 10 is designed to be assembled to a reservoir (not shown) in any known manner.

According to the invention, the device includes dispensing detector means 30, 31 which are adapted to detect the dispensing of one dose of fluid. The detector means 30, 31 are preferably adapted to deliver a signal used to inform the user that one dose of fluid has indeed been dispensed by said pump. The user can be informed in various ways, e.g. by means of a display device. In a variant, sound information means or similar information means could be used to indicate to the user that the dose has been dispensed. Advantageously, the signal emitted by the dispensing detector means 30 could also be used to actuate a dose counter. Thus, when the dispenser pump is a pump in which the dose is so finely sprayed that the user is not aware whether dispensing has taken place, the present invention makes it possible to avoid any risk of over-dosing by informing the user that the dose has indeed been dispensed.

In a first embodiment, said detector means comprise a dynamic pressure detector 30 for detecting when fluid goes from the pump 10 to the dispensing orifice 25.

Figure 2:
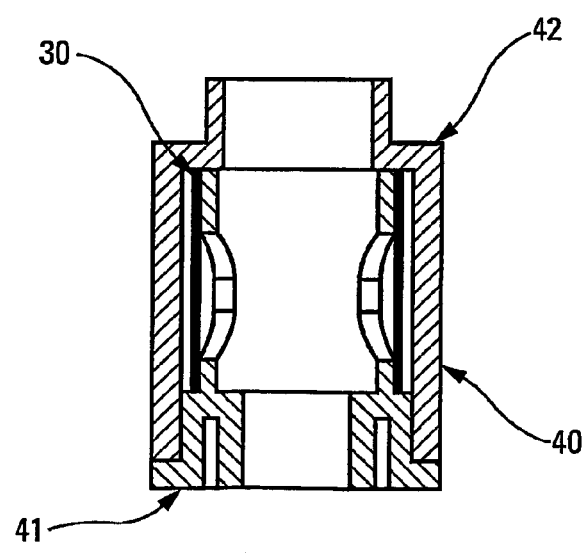
FIG. 2 is an enlarged detail view of a portion of FIG. 1.

The detector 30 preferably comprises a piezoelectric material, and advantageously polyvinylidene fluoride (PVDF) which is a plastics material that has piezoelectric properties. Advantageously, as shown in FIG. 2, the detector 30 comprises a PVDF tube operating in breathing mode.

This implementation guarantees detection that is completely reliable, even when very small quantities are expelled.

As shown in FIG. 1, the detector 30 can be disposed in the expulsion channel 50 that connects the dispenser pump 10 to the spray orifice 25 of the device. Advantageously, it is disposed in a sleeve 40 connected at one end to the actuator rod of the pump 10 and at the other end to the dispenser head 20. The sleeve 40 can be engaged around said actuator rod, and it can be made up of two portions 41, 42 fitted one on or around the other, the detector 30 being disposed between the two portions. This simplifies and facilitates assembly of the device, and makes it possible to guarantee leaktightness.

Figure 3:
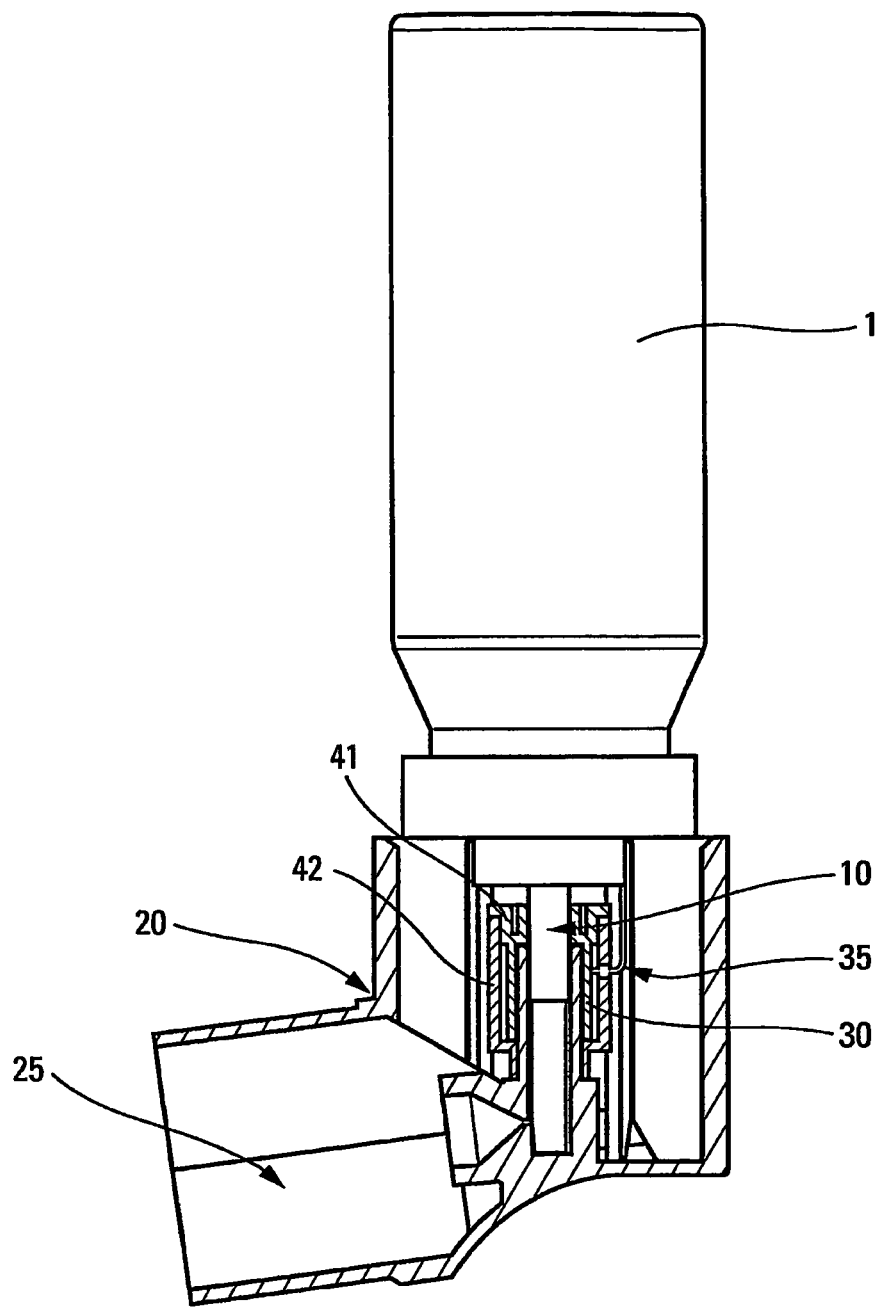
FIG. 3 is a view similar to the FIG. 1 view, showing a variant embodiment of the present invention.

FIG. 3 shows a variant embodiment in which the dispenser member is a valve 10, e.g. a metering valve operating in the upside down position. The detector 30 is implemented in a manner similar to the manner of the preceding example, namely in the form of a PVDF tube placed in a sleeve 40 made up of two portions 41, 42, and assembled around the valve member well of the valve. In this application, the fluid is generally an aqueous solution, it being possible for the maximum output pressure of the valve to be as high as 1000 kilopascals (kPa), i.e. 10 bars. This puts high stresses on the detector and on the sealing means, and the above-described structure makes it possible to adapt without any problem to accommodate such stresses and to guarantee that the dispenser device operates reliably, avoiding any under-counting and over-dosing, even in the event that the device is actuated partially.

Figure 4:
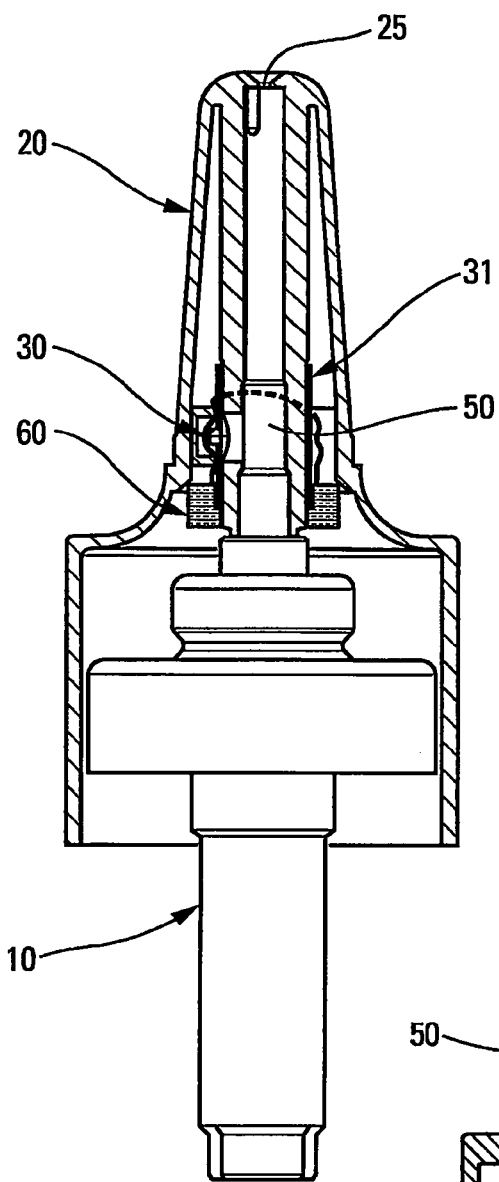
FIG. 4 is a view similar to the FIG. 1 view, showing another embodiment of the invention.
Figure 5:
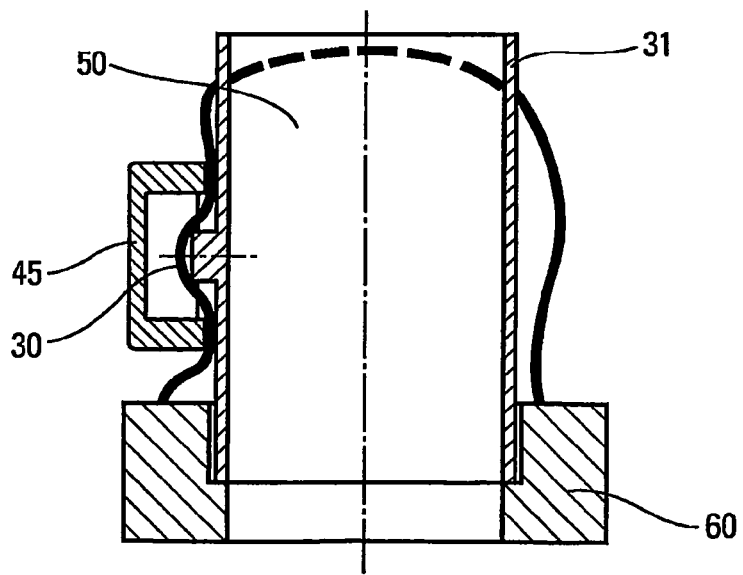
FIG. 5 is an enlarged detail view of a portion of FIG. 4.

FIG. 4 shows another embodiment of the invention, in which the detector means comprise a detector formed by an optical fiber 30. Said optical fiber is preferably associated with a deformable membrane 31, advantageously disposed around a portion of the expulsion channel 50. While the fluid is being expelled, the membrane 31 deforms, in particular under the effect of pressure, thereby generating stresses in the optical fiber 30, thereby generating a signal that is usable by suitable electronic means 60. Optical measurement is advantageous in terms of miniaturization insofar as an optical fiber that is compatible with plastics molding and/or overmolding techniques is used. Advantageously, the optical fiber 30 co-operates with the membrane 31 in a casing 45 which can be secured to the dispenser head 20, and in which the optical fiber 30 is retained securely in a manner such as to detect any deformation in the membrane 31. In this embodiment, the electrical means 60 can comprise a transmitter and a detector that is sensitive to variation in the light flux conveyed by the optical fiber 30, such variation being due to the stress generated in the fiber. The optical fiber can be made of plastic or of glass.

In general, the detector means 30, 31 can be connected, via suitable connection means 35, to electronic means 60 which are adapted to process the signal(s) delivered by said detector 30, so as to inform the user that the dose has been dispensed, and/or so as to actuate a dose counter or indicator.

Although the present invention is described above with reference to particular embodiments thereof, it should be understood that it is not limited by the examples shown in the figures. On the contrary, the person skilled in the art can make any necessary modifications without going beyond the present invention as defined by the accompanying claims.

The invention claimed is:

1. A fluid dispenser device including a fluid dispenser member (10) and a dispenser head (20) provided with a dispensing orifice, said fluid dispenser device being provided with dispensing detector means (30, 31) for detecting dispensing of a dose of fluid, said detector means (30, 31) being adapted to deliver a signal for informing the user that a dose of fluid has indeed been dispensed, said detector means comprising a detector (30) for detecting the fluid going from said dispenser member to said dispenser orifice, wherein said detector (30) comprises a piezoelectric material; and wherein said detector means are disposed in a sleeve co-operating at one end with said dispenser member and at the other end with said dispenser head; and said sleeve is made up of two portions engaged one on and surrounding at least in part the other, said detector means being disposed between said two sleeve portions, such that one sleeve portion contacts the dispenser member and not the dispenser head and the other sleeve portion contacts the dispenser head and not the dispenser member;

wherein the detector is tubular and surrounds an inner surface of the sleeve; wherein one of the two sleeve portions is radially outside the detector and the other of the two sleeve portions is radially inside the detector; and wherein the fluid dispenser member is a pump or a valve.

2. A device according to claim 1, in which the dispenser member (10) is connected to the dispensing orifice (40) via an expulsion channel (50), said detector means (30, 31) being provided in said expulsion channel (50).

3. A device according to claim 2, wherein the detector comprises a PVDF tube and in which said PVDF tube is disposed around a portion of said expulsion channel (50).

4. A device according to claim 1, in which said detector (30) is a dynamic pressure detector.

5. A device according to claim 1, in which said detector (30) comprises polyvinylidene fluoride (PVDF).

6. A device according to claim 1, in which said detector (30) comprises a PVDF tube operating in a breathing mode.

7. A device according to claim 1, wherein fluid dispenser member comprises a valve and in which said sleeve (40) is engaged around a valve member of the valve, or around an actuating rod of the dispenser member.

8. A device according to claim 1, in which said detector means (30, 31) are connected to electronic means (60) for processing the signals delivered by said detector means (30, 31).

9. A device according to claim 1, in which said detector means (30, 31) are adapted to increment or to decrement a dose counter.

10. A device according to claim 1, in which said dispenser member is a pump (10) and said detector means (30) informs the user every time a dose of fluid is dispensed.

11. A device according to claim 1, in which said dispenser member is a metering valve (10) operating with a propellant gas.

12. A fluid dispenser device, comprising:
a fluid dispenser member; and
a dispenser head provided with a dispensing orifice;
the fluid dispenser device comprises a detector that detects a dose of fluid going from the dispenser member to the dispenser orifice, the detector delivers a signal that informs the user that a dose of fluid has been dispensed by the dispenser member, the detector comprising a piezoelectric material; and
wherein the detector is disposed in a sleeve comprised of two sleeve portions coupled together, one sleeve portion surrounding at least in part the other; wherein one sleeve portion forms a fluid coupling with the dispenser member and the other sleeve portion forming a fluid coupling with the dispenser head, the detector located between the two sleeve portions; wherein one of the two sleeve portions contacts the dispenser member and not the dispenser head and the other of the two sleeve portions contacts the dispenser head not the dispenser member; wherein the detector is tubular and surrounds an inner surface of the sleeve; wherein one of the two sleeve portions is radially outside the detector and the other of the two sleeve portions is radially inside the detector; and wherein the fluid dispenser member is a pump or a valve.

13. The fluid dispenser device according to claim 12, wherein in the two sleeve portions overlap over a substantial axial length of the sleeve.

14. The fluid dispenser device according to claim 12, wherein the sleeve portion that forms the fluid coupling with the dispenser member extends axially at one end beyond the sleeve portion forming the fluid coupling with the dispenser head, and wherein the sleeve portion forming the fluid coupling with the dispenser head extends axially at one end beyond the sleeve portion that forms the fluid coupling with the dispenser member.

* * * * *